United States Patent [19]

Brunner

[11] Patent Number: 4,648,896
[45] Date of Patent: * Mar. 10, 1987

[54] 2-ARYL-4,6-DIHALOPYRIMIDINES AS ANTIDOTE FOR PROTECTING CULTIVATED PLANTS FROM PHYTOTOXIC DAMAGE CAUSED BY HERBICIDES

[75] Inventor: Hans-Georg Brunner, Lausen, Switzerland

[73] Assignee: Ciba-Geigy Corporation, Ardsley, N.Y.

[*] Notice: The portion of the term of this patent subsequent to Jan. 15, 2002 has been disclaimed.

[21] Appl. No.: 549,038

[22] Filed: Nov. 7, 1983

[30] Foreign Application Priority Data

Nov. 15, 1982 [CH] Switzerland ............... 6650/82

[51] Int. Cl.$^4$ ............ A01N 43/54; C07D 239/30; C07D 239/34; C07D 239/42
[52] U.S. Cl. ............................... 71/90; 71/92; 544/298; 544/319; 544/322
[58] Field of Search ............ 71/92; 544/298, 322

[56] References Cited

U.S. PATENT DOCUMENTS

| | | |
|---|---|---|
| 3,442,898 | 5/1969 | Luethi et al. ............ 260/251 |
| 3,445,466 | 5/1969 | Hahn et al. ............ 260/251 |
| 3,498,984 | 3/1970 | Santilli et al. ............ 260/256.5 |
| 3,503,976 | 3/1970 | Reichender et al. ............ 260/256.4 |
| 3,707,485 | 12/1972 | Gutsche et al. ............ 544/298 |
| 3,940,395 | 2/1976 | Santilli et al. ............ 260/256.5 R |
| 3,984,411 | 10/1976 | Claverie et al. ............ 544/298 |
| 4,084,053 | 4/1978 | Desai et al. ............ 544/184 |
| 4,297,234 | 10/1981 | Burdeska et al. ............ 252/301.24 |
| 4,412,074 | 10/1983 | Hoegerle et al. ............ 544/298 |
| 4,493,726 | 1/1985 | Burdeska et al. ............ 544/334 |

FOREIGN PATENT DOCUMENTS

| | | |
|---|---|---|
| 0055693 | 7/1982 | European Pat. Off. . |
| 2202820 | 7/1973 | Fed. Rep. of Germany . |
| 2182994 | 12/1973 | France . |
| 309033 | 7/1930 | United Kingdom . |

Primary Examiner—Donald G. Daus
Assistant Examiner—Stephen M. Kapner
Attorney, Agent, or Firm—Edward McC. Roberts; Irving M. Fishman

[57] ABSTRACT

2-Aryl-4,6-dihalopyrimidines of the formula I

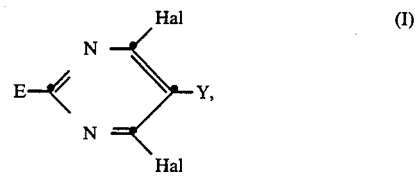

wherein
Hal is halogen,
E is unsubstituted or substituted phenyl, thienyl or furyl, and
Y is a group bound by way of nitrogen, oxygen or sulfur, are able as antidote or 'safener' to protect cultivated plants against the phytotoxic action of herbicides. Cultivated plants concerned are particularly sorghum, cereals, maize, rice and soya bean, and herbicides concerned are chloroacetanilides or other herbicidally effective substances.

25 Claims, No Drawings

2-ARYL-4,6-DIHALOPYRIMIDINES AS ANTIDOTE FOR PROTECTING CULTIVATED PLANTS FROM PHYTOTOXIC DAMAGE CAUSED BY HERBICIDES

The present invention relates to 2-aryl-4,6-dihalopyrimidines which are suitable as antidotes for protecting cultivated plants from phytotoxic damage caused by herbicides. The 2-aryl-4,6-dihalopyrimidines are applied to the cultivated crops simultaneously with, or shortly after, the application of the herbicide. There can also be used a composition containing both the herbicide and the 2-aryl-4,6-dihalopyrimidine; or the seeds or seed grain of the cultivated plants can be pretreated (dressed) with the 2-aryl-4,6-dihalopyrimidine, and the sown or emerged crops subsequently treated with the herbicide. The invention relates also to compositions containing the 2-aryl-4,6-dihalopyrimidines, as well as to the use thereof.

It is known that herbicides of the most varied classes of substances, such as triazines, urea derivatives, carbamates, thiolcarbamates, haloacetanilides, halophenoxyacetic acid, and so forth, can, when applied in effective amounts, sometimes damage to some degree the cultivated plants besides acting against the weeds to be controlled. Overdoses are often accidently applied along boundary areas when spraying is being carried out in strips, either as a result of the action of the wind or as a result of a wrong estimation of the spread effect of the spraying device being used. Climatic conditions and the nature of the soil can also play a part, so that the amount of herbicide recommended for normal conditions has the effect of an overdose. Furthermore, the quality of the seed with respect to its compatibility with the herbicide is also a factor to be taken into account. With the aim of overcoming this problem, there have already been suggested various substances which are capable of specifically antagonising the harmful action of a herbicide on the cultivated plants, that is to say, capable of protecting the cultivated plants without at the same time noticeably affecting the herbicidal action against the weeds to be controlled. It has however been shown that the suggested antidotes frequently have only a narrow field of action, both with respect to the cultivated plants and to the herbicide, and also with respect to the dependence of their action in some cases on the mode of their application, in other words, a specific antidote is suitable often for only a certain variety of cultivated plant and for only a few classes of herbicidal substances.

The 2-aryl-4,6-dihalopyrimidines correspond to the general formula I

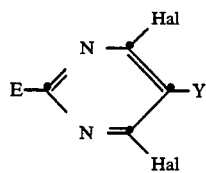

wherein
E is a group

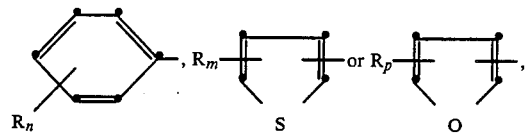

Hal each independently of the other is halogen, and
Y is a group: $-NR^1R^2$, $-OR^3$, $-SR^3$, $-SO-R^4$, $-SO_2-R^4$, $-N=CR^4R^5$, $-N=CH-NR^6R^7$, $-SCN$ or $-N(R^4)-CN$, in which
R is halogen, nitro, cyano, $-XR^8$, $-NR^9R^{10}$, $-CO-R^{11}$, $-COOR^{11}$, $-CO-NR^9R^{10}$, $-CS-NR^9R^{10}$, $-SO_2-NR^9R^{10}$, $-C(OR^{11})_2-R^{11}$,

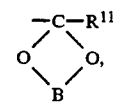

$-SO_3H$, $-N=CR^4R^5$, $-O-CO-N(R^{11})_2$, $-O-CO-N(R^{11})-OR^{11}$, a $C_1-C_6$-alkyl or $C_3-C_6$-cycloalkyl group each unsubstituted or substituted by halogen, $-XR^8$, $-NR^9R^{10}$, $-COR^{11}$, $-COOR^{11}$, $-CO-NR^9R^{10}$ or cyano, or is a $C_2-C_6$-alkenyl or $C_2-C_6$-alkynyl group each unsubstituted or substituted by halogen or $-XR^8$,
n is zero or a number from one to five,
m and p are zero or a number from one to four,
$R^1$, $R^2$ and $R^3$ independently of one another are each hydrogen, $-SO_2-$, $C_1-C_6$-alkyl, $-SO_2-C_1-C_6$-haloalkyl, $-CO-R^4$, $-COOR^4$, $-CON(R^4)_2$, $-CONHR^{12}$, $C_3-C_6$-alkynyl, or $C_1-C_6$-alkyl or $C_3-C_6$-alkenyl each unsubstituted or substituted by halogen or $C_1-C_4$-alkoxy, or
$R^1$ and $R^2$ together form a 4- to 6-membered alkylene chain which can be interrupted by oxygen, sulfur or an imino or $C_1-C_4$-alkylimino group,
$R^4$ and $R^5$ independently of one another are hydrogen, $C_3-C_6$-alkynyl, or $C_1-C_6$-alkyl or $C_3-C_6$-alkenyl each unsubstituted or substituted by halogen or $C_1-C_4$-alkoxy,
$R^6$ and $R^7$ independently of one another are each $C_1-C_6$-alkyl which is unsubstituted or substituted by halogen,
X is oxygen, sulfur, $-CO-$ or $-SO_2-$,
$R^8$ is hydrogen, $C_1-C_6$-alkylcarbonyl, $C_3-C_6$-alkenylcarbonyl, $C_3-C_6$-alkynylcarbonyl, or a $C_1-C_6$-alkyl, $C_3-C_6$-alkenyl or $C_3-C_6$-alkynyl group each unsubstituted or substituted by halogen, hydroxyl, $C_1-C_4$-alkoxy or $-NR^9R^{10}$,
$R^9$ and $R^{10}$ independently of one another are each hydrogen, $C_3-C_6$-alkenyl, $C_3-C_6$-alkynyl, $C_3-C_6$-cycloalkyl, or $C_1-C_6$-alkyl which is unsubstituted or substituted by $-CO-R^{11}$, $COOR^{11}$ or $-CO-NR^6R^7$, and also one of the two radicals can be $-OR^{11}$, $COOR^{11}$, $-CON(R^{11})$ or $-CO-N(R^{11})-OR^{11}$, or
$R^9$ and $R^{10}$ together can form a 4- to 6-membered alkylene chain which can be interrupted by oxygen or sulfur or by an imino or $C_1-C_4$-alkylimino group,
$R^{11}$ is hydrogen, or a $C_1-C_6$-alkyl, $C_3-C_6$-alkenyl or $C_3-C_6$-alkynyl group each unsubstituted or substituted by halogen, hydroxyl, $C_1-C_4$-alkoxy or $-NR^4R^5$,
$R^{12}$ is a phenyl group

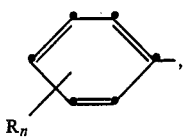

and

B is a branched-chain or straight-chain $C_1$-$C_6$-alkyl chain.

By alkyl in the definitions is meant straight-chain or branched-chain alkyl, for example: methyl, ethyl, n-propyl, i-propyl, the four isomeric butyl groups, n-amyl, i-amyl, 2-amyl, 3-amyl, n-hexyl or i-hexyl.

By alkoxy is meant: methoxy, ethoxy, n-propyloxy, i-propyloxy and the four isomeric butyloxy groups, especially however methoxy, ethoxy or i-propoxy.

Examples of alkenyl groups are: vinyl, allyl, isopropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, particularly vinyl, allyl and 4-pentenyl.

By halogen in the definitions, as well as in haloalkyl, haloalkoxy, haloalkylsulfinyl, haloalkylsulfonyl and haloalkylthio, are meant fluorine, chlorine and bromine, preferably however fluorine and chlorine.

Alkynyl groups in the definitions of the above symbols are as a rule: propargyl, 2-butynyl, 3-butynyl, as well as isomeric pentynyl or hexynyl groups; preferably however the alkynyl group is propargyl or 2- or 3-butynyl.

Cycloalkyl within the scope of the present application is cyclopropyl, cyclobutyl, cyclopentyl and cyclohexyl.

Heterocycles which can be formed by the radicals $R^1$ and $R^2$ or $R^9$ and $R^{10}$ together with the nitrogen atom are preferably pyrrolidine, piperidine, morpholine and thiomorpholine.

By halogen as substituent of the pyrimidine nucleus is meant fluorine, chlorine or bromine, particularly however chlorine.

Preferred compounds are those in which Hal denotes simultaneously two identical halogen substituents.

A preference in the case of some active substances of the formula I is that E is

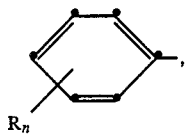

wherein R and n have the meanings defined under the formula I.

Likewise preferred are those compounds of the formula I in which E is one of the groups

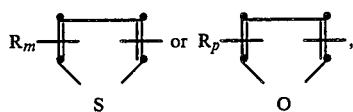

wherein R has the meaning defined under the formula I, and m and p are each zero or the number one or two.

Preferred compounds among the compounds of the formula I in which E is the phenyl group are on the other hand those wherein n is zero, one or two, and R is halogen, nitro, cyano, $-XR^8$, $-NR^9R^{10}$, $-CO-R^{11}$, $-COOR^{11}$, $-CO-NR^9R^{10}$, $C_1$-$C_4$-alkyl, $C_2$-$C_4$-alkenyl or $C_2$-$C_4$-alkynyl, the symbols $R^8$, $R^9$, $R^{10}$ and $R^{11}$ having the meanings defined under the formula I.

Preferred amongst the last-mentioned compounds are also those in which Hal is chlorine or bromine.

A particularly preferred subgroup of compounds of the formula I, is formed by the compounds in which E is a phenyl nucleus which is unsubstituted or is monosubstituted by methoxy, fluorine, hydroxyl, methyl, ethynyl, carboxyl, acetyl, nitro, amino, dimethylamino, acetamido or methylaminocarbonyloxy, or is disubstituted by fluorine or chlorine, or is trisubstituted by methoxy, Hal is chlorine or bromine, and Y is $-NR^1R^2$, $-OR^3$, $-SR^3$, $-N=CH-NR^6R^7$ or $-N=CR^4R^5$, the symbols $R^1$ to $R^7$ having the meanings defined under the formula I.

Compounds of the formula I to be particularly emphasised are those in which E is phenyl, Hal is chlorine, and Y is amino, dimethylamino, diacetamido, trifluoroacetamido, hydroxyl, methoxy, methylthio, acetoxy, acetamido or methylaminocarbonyloxy.

Preferred individual compounds to be mentioned are: 5-amino-4,6-dichloro-2-phenylpyrimidine, 4,6-dichloro-5-methoxy-2-phenylpyrimidine, and 4,6-dichloro-5-hydroxy-2-phenylpyrimidine.

The 2-aryl-4,6-dihalopyrimidines of the formula I are excellently suitable for protecting cultivated plants, such as millet, rice, maize, varieties of cereals (wheat, rye, barley, oats, and so forth), cotton, sugar beet, sugar cane, soya bean, and the like, against the phytotoxic action of herbicides of the most varied classes of substances, such as triazines, phenylurea derivatives, carbamates, thiolcarbamates, haloacetanilides, halophenoxyacetic acid esters, substituted phenoxyphenoxyacetic acid esters and -propionic acid esters, substituted pyridineoxyphenoxyacetic acid esters and -propionic acid esters, benzoic acid derivatives, and so forth, in so far as these do not act selectively or sufficiently selectively, that is to say, damage to a lesser or greater extent the cultivated plants as well as acting against the weeds to be controlled. The present invention relates also to compositions containing these 2-aryl-4,6-dihalopyrimidines of the formula I together with the herbicides.

There have already been suggested, as antidotes, various substances which are able to specifically antagonise the harmful action of a herbicide on the cultivated plants, that is to say, able to protect the cultivated plants without at the same time to noticeably reduce the herbicidal action against the weeds to be controlled. Depending on its properties, an antidote of this type, known also as 'safener', can be used for the pretreatment of the seed of the cultivated plant (dressing of the seed or seedlings), or can be introduced into the seed furrows before sowing, or can be used as a tank mixture together with the herbicide, before or after the emergence of the plants.

The G.B. Patent Specification No. 1,277,557 describes for instance the treatment of seeds or shoots of wheat and millet with certain oxamic acid esters and amides for protection against an attack by N-methoxymethyl-2',6'-diethyl-chloroacetanilide (Alachlor). In other publications (German Offenlegungsschriften Nos. 1,952,910 and 2,245,471 and French Patent Specification No. 2,021,611), there are suggested antidotes for the treatment of the seeds of cereals, maize and rice to protect them against the attack by herbicidal thiolcarbamates. In the German Patent Specification No. 1,576,676 and in the U.S. Pat. No. 3,131,509, hydroxyamino-acetanilides and hydantoins are suggested for the protection of cereal seed against carbamates, such as IPC, CIPC, and so forth. In further development, however, all these preparations have proved to be inadequate. And phenylpyrimidines having a safener action have recently been described in the European Patent Application No. 55693.

2-Aryl-4,6-dihalopyrimidines of the formula I surprisingly have the property of being able to protect cultivated plants against attack by aggressive agricultural chemicals, particularly herbicides of the most varied classes of substances, for example chloroacetanilides, chloroacetamides, carbamates and thiocarbamates, diphenyl ethers and nitrodiphenyl ethers, benzoic acid derivatives, triazines and triazinones, phenylureas, nitroanilines, oxdiazolones, pyridyloxyphenoxy derivatives, phosphates and pyrazoles, in so far as these are not tolerant or insufficiently tolerant towards cultivated plants.

The cultivated plants are protected by the 2-aryl-4,6-dihalopyrimidines according to the invention particularly against the herbicides of the following classes classes: chloroacetanilides, chloroacetamides, thiocarbamates and phosphates.

Depending on the purpose of application, such an antidote of the formula I can be used for the pretreatment of the seed or seedlings of the cultivated plant (dressing of the seed or of cuttings), or can be introduced into the soil before or after sowing, or can be applied on its own or together with the herbicide before or after emergence of the plants. The treatment of the plant or of the seed or seedlings with the antidote can be carried out therefore essentially independently of the time of application of the phytotoxic chemical. It can however be carried out simultaneously (tank mixture). The pre-emergence treatment includes both the treatment of the cultivated area before sowing (ppi="pre plant incorporation") and the treatment of the sown cultivated area before emergence of the plants.

The applied amounts of antidote in proportion to the herbicide depend largely on the mode of application. In the case of a field treatment, which is carried out either with the use of a tank mixture or with a separate application of herbicide and antidote, the employed ratio of antidote to herbicide is as a rule from 1:100 to 10:1, preferably however the range is 1:5 to 8:1, especially 1:1.

With seed dressing and similar specific protective measures, however, the amounts of antidote required compared with for example the amounts of herbicide which would be applied later per hectare of cultivated land are much smaller. There are used for seed dressing as a rule 0.1 to 10 g of antidote per kg of seed, the amount preferred being between 1 and 2 g. When the antidote is to be applied shortly before sowing, by seed soaking, there are preferably used for example antidote solutions containing the active ingredient at a concentration of 1–10,000 ppm, particularly 100–1000 ppm.

Protective measures such as seed dressing with an antidote of the formula I and possible subsequent field treatment with agricultural chemicals are as a rule separated by a considerable interval of time. Pretreated seed and plant material can come into contact later, in agriculture, horticulture and forestry, with various chemicals. The present invention relates therefore also to compositions for protecting cultivated plants, which compositions contain as active ingredient an antidote of the formula I together with customary carriers. These preparations can if required be additionally mixed with the agricultural chemicals against which the cultivated plant is to be protected, for example with a herbicide.

Cultivated plants applying within the scope of the present invention are all those which in some form produce productive materials (seeds, roots, stalks, tubers, leaves, flowers, or components such as oils, sugar, starch, protein, and so forth), and which for this purpose are cultivated and preserved. These plants include for example all varieties of cereals, wheat, rye, barley and oats, in addition particularly rice, cultivated millet and maize, as well as cotton, sugar beet, sugar cane, soyabean, beans, peas, and the like.

The antidote of the invention is to be used in all cases where a cultivated plant has to be protected against the phytotoxicity of a chemical.

The following are for example listed as herbicides against the action of which the cultivated plants have to be protected:

chloroacetanilides:
2-chloro-2',6'-diethyl-N-(2''-propyloxyethyl)-acetanilide ("Pretilachlor"), 2-chloro-6'-ethyl-N-(2''-methoxy-1''-methylethyl)-acet-o-toluidide ("Metolachlor"), 2-chloro-2',6'-diethyl-N-(butoxymethyl)-acetanilide ("Butachlor"), 2-chloro-6'-ethyl-N-(ethoxymethyl)-acet-o-toluidide ("Acetochlor"), 2-chloro-6'-ethyl-N-(2''-propoxy-1''-methylethyl)-acet-o-toluidide, 2-chloro-2',6'-dimethyl-N-(2''-methoxy-1''-methylethyl)-acetanilide, 2-chloro-2',6'-dimethyl-N-(2''-methoxyethyl)-acetanilide ("Dimethachlor"), 2-chloro-2',6'-diethyl-N-(pyrazol-1-ylmethyl)-acetanilide, 2-chloro-6'-ethyl-N-(pyrazol-1-ylmethyl)-acet-o-toluidide, 2-chloro-6'-ethyl-N-(3,5-dimethyl-pyrazol-1-ylmethyl)-acet-o-toluidide, 2-chloro-6'-ethyl-N-(2''-butoxy-1''-methylethyl)-aceto-o-toluidide ("Metazolachlor"), 2-chloro-6'-ethyl-N-(2''-butoxy-1''-(methylethyl)-acet-o-toluidide, 2-chloro-2'-trimethylsilyl-N-(butoxymethyl)-acetanilide, 2-chloro-2',6'-diethyl-N-(methoxymethyl)-acetanilide ("Alachlor"), 2-chloro-2',6'-diethyl-N-(ethoxycarbonylmethyl)-acetanilide, 2-chloro-N-(2''-n-propoxyethyl)-2',6'-acetoxylide, 2-chloro-6'-ethyl-N-(2''-n-propoxyethyl)-acet-o-toluidide, 2-chloro-N-isopropyl-3',3',5'-trimethyl-acetanilide, 2-chloro-6'-tert-butyl-N-(n-butoxymethyl)-acet-o-toluidide ("Terbuchlor), 2-chloro-N-(isobutoxymethyl)-2',6'-acetoxylide and 2-chloro-N-(sec-butoxymethyl)-2',6'-acetoxylide;

chloroacetamides:
N-[1-isopropyl-2-methylpropen-1-yl-(1)-N-(2'-methoxyethyl)-chloroacetamide, 2-chloro-N-(n-butoxymethyl)-2',6'-dimethyl-1'-cyclohexeneacetamide and N-isopropyl-2-chloro-N-(3,3,5-trimethyl-1-cyclohexen-1-yl-chloroacetamide;

carbamates and thiocarbamates:
N-(3',4'-dichlorophenyl)propionanilide ("Propanil"), S-4-chlorobenzyl-diethylthiocarbamate ("Benthiocarb"), S-ethyl-N,N-hexamethylenethiocarbamate ("Molinate"), S-ethyl-dipropyl-thiocarbamate ("EPTC"), N,N-di-sec-butyl-S-benzyl-thiocarbamate (Drepamon), S-(2,3-dichlorallyl)-di-isopropylthiocarbamate and S-(2,3,3-trichlorallyl)-di-isopropylthiocarbamate ("Di- and Tri-allate"), 1-(propylthiocarbonyl)-decahydro-quinaldine, S-4-benzyldiethylthiocarbamate, as well as corresponding sulfinylcarbamates;

dimedones:

2-[1-(ethoxyimino)-butyl]-5-(ethylthio)-propyl-3-hydroxy-2-cyclohexen-1-one ("Sethoxydin") and the Na salt of 2-[1-(N-allyloxamino)-butylidene]-5,5-dimethyl-4-methoxycarbonyl-cyclohexane-1,3-dione ("Alloxidimedon");

diphenyl ethers and nitrodiphenyl ethers:
2,4-dichlorophenyl-4'-nitrophenyl ether ("Nitrofen"), 2-chloro-1-(3'-ethoxy-4'-nitrophenoxy)-4-trifluoromethyl-benzene ("Oxyfluorfen"), 2',4'-dichlorophenyl-3-methoxy-4-nitrophenyl ether ("Chlormethoxinyl"), 2-[4'-(2",4"-dichlorophenoxy)-phenoxy)-propionic acid methyl ester, N-(2'-methoxyethyl)-2-[5'-(2"-chloro-4"-trifluoromethylphenoxy)-phenoxy]-propionic acid amide, α-[4-(2,4-dichlorophenoxy)-phenoxy]-propionic acid methyl ester ("Hoelon"), α-[4-(5'-trifluoromethylpyridyl-2'-oxy)-phenoxy]-propionic acid-n-butyl ester ("Fluazifop-butyl") and α-[4-(3',5'-dichloropyridyl-2'-oxy)-phenoxy]-propionic acid propyl ester ("Chlorazifop-propinyl");

benzoic acid derivatives:
methyl-5-(2',4'-dichlorophenoxy)-2-nitrobenzoate ("Bifenox"), 5-(2'-chloro-4'-trifluoromethylphenoxy)-2-nitrobenzoic acid ("Acifluorfen") and 2,6-dichlorobenzonitrile ("Dichlobenil");

triazines and triazinones:
2,4-bis(isopropylamino)-6-methylthio-1,3,5-triazine ("Prometryn"), 2,4-bis(ethylamino)-6-methylthio-1,3,5-triazine ("Simetryn"), 2-(1',2'-dimethylpropylamino)-4-ethylamino-6-methylthio-1,3,5-triazine ("Dimethametryn") and 4-amino-6-tert-butyl-4,5-dihydro-3-methylthio-1,2,4-triazin-5-one ("Metribuzin");

phenylureas:
N-(3'-isopropylphenyl)-N',N'-dimethylurea ("Isoproturon"), N-(3',4'-dimethylbenzyl)-N'-4-tolylurea ("Dimuron") and N-(3'-chloro-4'-isopropylphenyl)-N',N'-(3-methyl-pentamethylen-1,5-yl)-urea;

nitroanilines:
2,6-dinitro-N,N-dipropyl-4-trifluoromethylaniline ("Trifluralin"), N-(1'-ethylpropyl)-2,6-dinitro-3,4-xylidine ("Pendimethalin");

oxadiazolones:
5-tert-butyl-3-(2',4'-dichloro-5'-isopropoxyphenyl)-1,3,4-oxadiazol-2-one ("Oxdiazon");

pyridyloxyphenoxy derivatives:
2-[4'-(3",5"-dichloropyridyl-2"-oxy)phenoxy]-propionic acid-(2-propynyl)ester; phosphates:

S-2-methylpiperidino-carbonylmethyl-O,O-dipropyl-phosphorodithioate ("Piperophos"); and pyrazoles:
1,3-dimethyl-4-(2',4'-dichlorobenzoyl)-5-(4'-tolylsulfonyloxy)-pyrazole;

diverse:
2-ethoxy-2,3-dihydro-3,3-dimethylbenzofuran-5-yl-methanesulfonate ("Ethofumesat") and benzothiazol-(2)-yl-oxy-acetic acid-N-methylanilide.

The 2-aryl-4,6-dihaloprimidine of the formula I or the composition containing this antidote can be applied either before or after application of the herbicide, or it can be applied simultaneously with the herbicide. The treatment of the seed with a solution containing the antidote (seed dressing) has proved particularly efficient. The procedure is either to evaporate off the solvent and to apply the seed dry with an antidote coating around it, or to pre-soak the seed in an aqueous solution containing the antidote and to sow the seed in this condition, as is the customary practice in the case of rice.

The 2-aryl-4,6-dihalopyrimidines of the formula I are obtained, in a manner known per se, by reacting an arylamidine of the formula II

wherein E has the meaning defined under the formula I, in the presence of a base, with a malonic acid derivative of the formula III

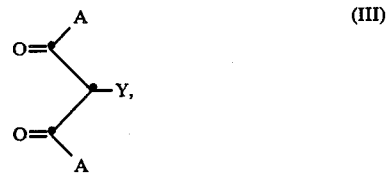

wherein Y has the meaning defined under the formula I, and A is amino or $C_1$-$C_6$-alkoxy, and converting the resulting 4,6-dihydroxypyrimidine of the formula IV

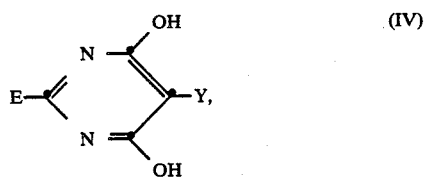

wherein E and Y have the meanings defined under the formula I, with a halogenating agent into the compound of the formula I.

Analogous processes are known from the European Patent Publication No. 55693.

Suitable bases to be mentioned are: hydroxides, such as NaOH or KOH; oxides, such as CaO or MgO; carbonates, such as $Na_2CO_3$, $K_2CO_3$, $CaCO_3$ or $MgCO_3$; hydrogen carbonates, such as $NaHCO_3$, $KHCO_3$ or $Ca(HCO_3)_2$; alcoholates, such as $NaOCH_3$, $NaOC_2H_5$, $NaOC_4H_9$-t, $NaOC_3H_7$-i, $KOCH_3$, $KOC_2H_5$, $KOC_4H_9$-t or $KOC_3H_7$-i. Examples of halogenating agents are: $SOCl_2$, $SOBr_2$, $PCl_3$, $PBr_3$, $PCl_5$, $PBr_5$, $POCl_3$ or $POBr_3$. The process according to the invention can be performed in both stages at temperatures of between 0° and 150° C., preferably between 20° and 120° C. It is particularly advantageous in carrying out the reaction to heat the mixture to reflux. The first reaction step is performed with advantage in an inert solvent, whereas the second step is usually performed without solvent, provided that the chlorinating agent is liquid and can be used in excess. Suitable solvents for the first step are alcohols, such as methanol, ethanol, propanol and isopropanol; hydrocarbons, such as benzene, toluene and xylene; ethers, such as diethyl ether, ethylene glycol dimethyl ether, diethylene glycol dimethyl ether, dioxane or tetrahydrofuran; ketones, such as acetone, ethyl methyl ketone or cyclohexanone, or dimethyl sulfoxide; especially however alcohols such as methanol and ethanol. Suitable solvents for the second step are hydrocarbons such as benzene, toluene, xylene or cyclohexane, and also the various ligroin fractions or the aforementioned ethers.

Individual subgroups of the compounds of the formula I can be produced, by processes known per se, from individual key compounds. Thus, the compounds of the formula I in which Y denotes the group —NR$^1$R$^2$, —N=CR$^4$R$^5$, —N=CH—NR$^6$R$^7$ or —N(R$^4$)—CN can be obtained by converting the amino compound produced according to the reaction schemes 1 and 2, using generally known methods, into the other derivatives.

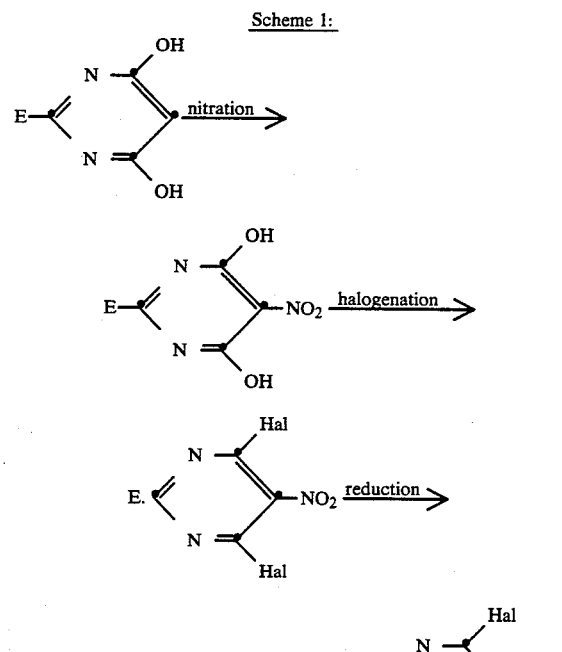

Scheme 1:

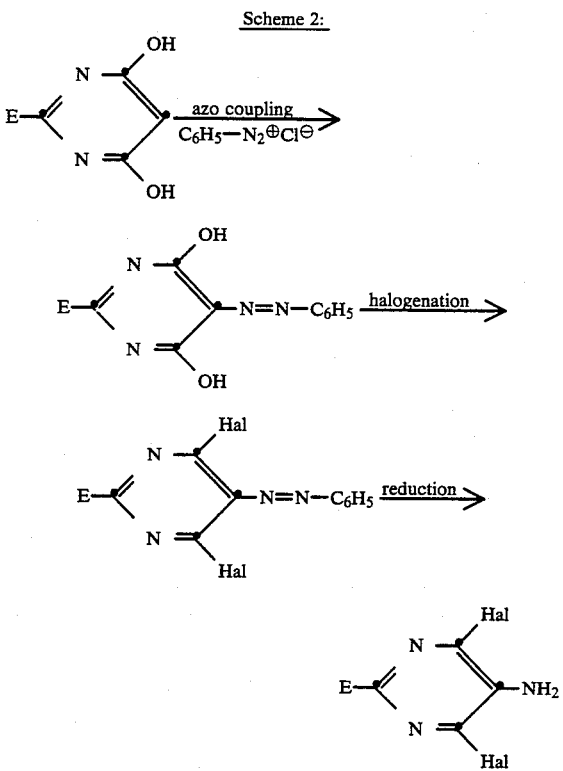

Scheme 2:

The compounds of the formula I in which Y is —OR$^3$, —SR$^3$, —SOR$^4$, —SO$_2$R$^4$ or —SCN can be obtained by conversion of corresponding hydroxyl and mercapto compounds, using generally known methods, into the stated derivatives. The 5-hydroxyl- and 5-mercaptopyrimidines of the formula I are for their part obtainable by ether cleavage from the corresponding 6-alkoxy- and 5-alkylthio compounds.

The 2-aryl-4,6-dihalopyrimidines of the formula I can be used on their own or together with the herbicides to be antagonised.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are, aromatic hydrocarbons, preferably the fractions C$_8$ to C$_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials or inorganic or organic nature, such as in particular dolomite or ground plate residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids (C$_{10}$–C$_{22}$), for example the Na or K salts of oleic or stearic acid, or of natural fatty acid mixtires, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included amongst these are also the salts of sulfuric acid esters and sulfonic acids of fatty alcohol ethylene oxide adducts. The sulfonated benzimidazole derivatives preferably contain 2 sulfonic acids groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)-ethylammonium bromide.

The tensides customarily used in formulation practice are described, inter alia, in the following publications:
 "Mc Cutcheon's Detergents and Emulsifiers Annual", MC Publishing Corp., Ridgewood, N.J. 1979;
 M. and J. Ash, "Encyclopedia of Surfactants", Vol. I–III, Chemical Publishing Co., Inc. New York 1980–1981;
 H. Stache, "Tensid Taschenbuch", 2nd Edition, C. Hauser Verlag, Munich and Vienna, 1981.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25%, of a tenside.

Whereas commercial products are preferably in the form of concentrated compositions, the compositions employed by the end-user are as a rule diluted.

The compositions can also contain further additives such as stabilisers, antifoam agents, viscosity regulators, binders and adhesives, as well as fertilisers or other active substances for obtaining special effects.

Percentages and parts in the following Examples relate to weight.

Production Examples

EXAMPLE 1

5-Amino-4,6-dichloro-2-phenylpyrimidine

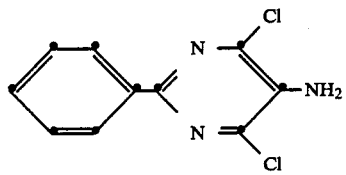

(a) To 500 ml of concentrated nitric acid at 0° C. are added, within 12 minutes, 147 g of 4,6-dihydroxy-2-phenylpyridine. The reaction solution was stirred for a further 10 minutes at 0° C., and is subsequently taken up in 2 liters of ice-water. The product which precipitates is separated, washed with water and dried. The yield is 158.5 g of 4,6-dihydroxy-5-nitro-2-phenylpyrimidine, m.p. 328°–333° C.

(b) A mixture of 46.6 g of 4,6-dihydroxy-5-nitro-2-phenylpyrimidine, 48 ml of N,N-dimethylaniline, 42 ml of phosphorus oxychloride and 270 ml of toluene is refluxed for 40 minutes. The excess solvent is afterwards evaporated off; the residue is then taken up in methylene chloride and washed twice with ice-water. The yield after drying and concentration of the organic phase by evaporation is 41.0 g of 4,6-dichloro-5-nitro-2-phenylpyrimidine.

(c) 27.0 g of 4,6-dichloro-5-nitro-2-phenylpyrimidine are hydrogenated in ether acetate at room temperature by treatment with Raney nickel. The catalyst is afterwards separated and the reaction solution is concentrated by evaporation. Crystallisation of the residue from petroleum ether then yields 17.4 g of 5-amino-4,6-dichloro-2-phenylpyrimidine, m.p. 143°–144° C. (compound No. 1).

EXAMPLE 2

4,6-Dichloro-5-dimethylamino-2-phenylpyrimidine

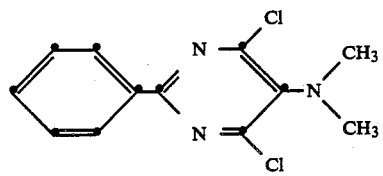

(a) To a solution of 30.5 g of 2-dimethylaminomalonic acid diethyl ester and 20.0 g of benzamidine in 80 ml of methanol are added dropwise 72.0 ml of a 30% sodium methylate solution, and the mixture is then refluxed for 6 hours. After the solvent has been evaporated off, the residue is taken up in 700 ml of water and washed with toluene. The aqueous phase is acidified with glacial acetic acid to a pH value of 5; the product which has precipitated is subsequently separated, washed and dried. The yield is thus 24.3 g of 5-dimethylamino-4,6-dihydroxy-2-phenylpyrimidine, m.p. >295° C.

(b) 6.9 g of 5-dimethylamino-4,6-dihydroxy-2-phenylpyrimidine in 25 ml of phosphorus oxychloride are refluxed for 2½ hours. After distilling off the excess phosphorus oxychloride, the residue is taken up in an ethyl acetate/ice-water mixture, and neutralised with sodium hydrogen carbonate to a pH value of 6–7. The organic phase is washed with water, dried, and concentrated by evaporation. The yield is 4.2 g of 4,6-dichloro-5-dimethylamino-2-phenylpyrimidine, m.p. 49°–50° C. (compound No. 3).

EXAMPLE 3

4,6-Dichloro-5-methoxy-2-phenylpyrimidine

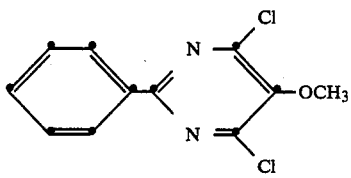

(a) A solution of 20.5 ml of benzonitrile in 50 ml of methanol is saturated at 0°–15° C. with gaseous hydrogen chloride, and stirred at 20°14 25° C. for 18 hours. The excess hydrogen chloride is subsequently expelled with nitrogen gas, and to the solution are added dropwise 50 ml of 10N methanolic ammonia solution. After the mixture has been refluxed for 1 hour, 26.4 g of 2-methoxymalonic acid diamide and 108 ml of 30% sodium methylate solution are added, and the mixture is again refluxed this time for 6 hours. The mixture is concentrated by evaporation; the residue is then dissolved in 250 ml of water, and washed with methylene chloride. After the mixture has been acidified with acetic acid, the product which precipitates is separated, washed and dried. The yield is 23.2 g of 4,6-dihydroxy-5-methoxy-2-phenylpyrimidine, m.p.>265° C. (decomp.).

(b) A mixture of 10.9 g of 4,6-dihydroxy-5-methoxy-2-phenylpyrimidine, 12.6 ml of N,N-dimethylaniline, 10 ml of phosphorus oxychloride and 50 ml of toluene is refluxed for 2 hours. After the mixture has been concentrated by evaporation, the residue is taken up in ethyl acetate, washed twice with 1N hydrochloric acid and twice with water, dried, and concentrated by evaporation. The yield is 10.2 g of 4,6-dichloro-5-methoxy-2-phenylpyrimidine, m.p. 78°–80° C. (compound No. 31).

EXAMPLE 4

4,6-Dichloro-5-hydroxy-2-phenylpyrimidine

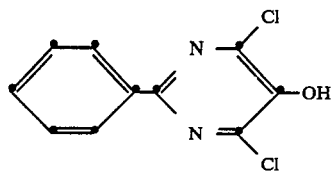

15.3 g of 4,6-dichloro-5-methoxy-2-phenylpyrimidine and 30 ml of 25% boron trichloride solution in methylene chloride are heated at 40° C. in a bomb tube for 15 hours. The reaction mixture is subsequently added dropwise to a mixture of methanol and methylene chloride (1:1), and then diluted with ice-water. The organic phase is separated, and the aqueous phase is extracted with methylene chloride. The combined organic phases are concentrated by evaporation and chromatographed on silica gel to thus obtain 8.7 g of 4,6-dichloro-5-hydroxy-2-phenylpyrimidine, m.p. 138°–140° C. (compound No. 34).

EXAMPLE 5

5-Acetoxy-4,6-dichloro-2-phenylpyrimidine

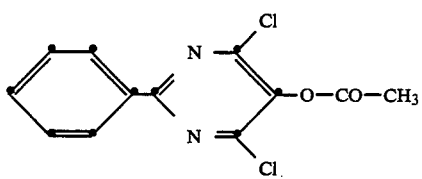

A solution of 3.1 g of 4,6-dichloro-5-hydroxy-2-phenylpyrimidine, 2.8 ml of trimethylamine, 1.6 ml of acetic anhydride and 0.1 g of 4-dimethylaminopyrimidine in 50 ml of toluene is stirred for 4 hours at 20°–25° C. The reaction solution is subsequently diluted with ethyl acetate, washed with water and dried. On concentration by evaporation, there crystallise 4.3 g of 5-acetoxy-4,6-dichloro-2-phenylpyrimidine, m.p. 145°–147° C. (compound No. 36).

The final products listed in the Table which follows are obtained in an analogous manner.

TABLE 1

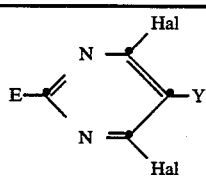

| No. | E | Y | Hal | Physical data |
|---|---|---|---|---|
| 1 | C$_6$H$_5$ | NH$_2$ | Cl, Cl | m.p. 143–144° C. |
| 2 | C$_6$H$_5$ | —NH—CH$_3$ | Cl, Cl | m.p. 71–72° C. |
| 3 | C$_6$H$_5$ | —N(CH$_3$)$_2$ | Cl, Cl | m.p. 49–50° C. |
| 4 | C$_6$H$_5$ | —NH—CH$_2$—CH=CH$_2$ | Cl, Cl | |
| 5 | C$_6$H$_5$ | N—Pyrrolidinyl | Cl, Cl | m.p. 68–73° C. |
| 6 | C$_6$H$_5$ | —NH—(CH$_2$)$_2$—OCH$_3$ | Cl, Cl | |
| 7 | C$_6$H$_5$ | —NH—(CH$_2$)$_2$—Cl | Cl, Cl | |
| 8 | C$_6$H$_5$ | —NH—CH$_2$—C≡CH | Cl, Cl | |
| 9 | C$_6$H$_5$ | —NH—CN | Cl, Cl | |
| 10 | C$_6$H$_5$ | —NH—CO—CH$_3$ | Cl, Cl | m.p. 216–218° C. |

TABLE 1-continued

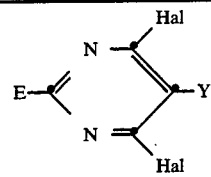

| No. | E | Y | Hal | Physical data |
|---|---|---|---|---|
| 11 | $C_6H_5$ | $-N(COCH_3)_2$ | Cl, Cl | m.p. 104–106° C. |
| 12 | $C_6H_5$ | $-NH-CO-CH_2Cl$ | Cl, Cl | |
| 13 | $C_6H_5$ | $-NH-CO-CF_3$ | Cl, Cl | m.p. 174–177° C. |
| 14 | $C_6H_5$ | $-NH-CO-CH=CH_2$ | Cl, Cl | |
| 15 | $C_6H_5$ | $-NH-CO-NH-CH_3$ | Cl, Cl | |
| 16 | $C_6H_5$ | $-NH-CO-NH-C_4H_9-n$ | Cl, Cl | |
| 17 | $C_6H_5$ | $-NH-CO-N(CH_3)_2$ | Cl, Cl | |
| 18 | $C_6H_5$ | $-NH-CO-N(CH_3)OCH_3$ | Cl, Cl | |
| 19 | $C_6H_5$ | $-N(CH_3)-CO-N(CH_3)OCH_3$ | Cl, Cl | |
| 20 | $C_6H_5$ | $-NH-CO-OCH_3$ | Cl, Cl | |
| 21 | $C_6H_5$ | $-NH-CO-O-CH=CH_2$ | Cl, Cl | |
| 22 | $C_6H_5$ | $-N(CH_3)-CO-OCH_3$ | Cl, Cl | |
| 23 | $C_6H_5$ | $-NH-SO_2-CH_3$ | Cl, Cl | |
| 24 | $C_6H_5$ | $-NH-SO_2-CF_3$ | Cl, Cl | |
| 25 | $C_6H_5$ | $-N(CH_3)-CO-CF_3$ | Cl, Cl | m.p. 135–137° C. |
| 26 | $C_6H_5$ | $-N=CH-N(CH_3)_2$ | Cl, Cl | |
| 27 | $C_6H_5$ | $-N=CH-CH_3$ | Cl, Cl | |
| 28 | $C_6H_5$ | $-N=CH-C_3H_7-i$ | Cl, Cl | |
| 29 | $C_6H_5$ | $-NH-CHO$ | Cl, Cl | |
| 30 | $C_6H_5$ | $-NH-C_3H_7-i$ | Cl, Cl | |
| 31 | $C_6H_5$ | $-OCH_3$ | Cl, Cl | m.p. 78–80° C. |
| 32 | $C_6H_5$ | $-O-CH_2-CH=CH_2$ | Cl, Cl | |
| 33 | $C_6H_5$ | $-O-CH_2-C\equiv CH$ | Cl, Cl | |
| 34 | $C_6H_5$ | OH | Cl, Cl | m.p. 138–140° C. |
| 35 | $C_6H_5$ | $-O-CH_2-CH_2Cl$ | Cl, Cl | |
| 36 | $C_6H_5$ | $-O-CO-CH_3$ | Cl, Cl | m.p. 145–147° C. |
| 37 | $C_6H_5$ | $-O-CO-CH_2Cl$ | Cl, Cl | |
| 38 | $C_6H_5$ | $-O-CO-C_2H_5$ | Cl, Cl | |
| 39 | $C_6H_5$ | $-O-CO-C_5H_{11}-n$ | Cl, Cl | |
| 40 | $C_6H_5$ | $-O-CO-CH=CH-CH_3$ | Cl, Cl | |
| 41 | $C_6H_5$ | $-O-CO-C_4H_9-i$ | Cl, Cl | |
| 42 | $C_6H_5$ | $-O-CO-NH-CH_3$ | Cl, Cl | m.p. 240° C. (decomp.) |
| 43 | $C_6H_5$ | $-O-CO-NH-C_4H_9-n$ | Cl, Cl | |
| 44 | $C_6H_5$ | $-O-CO-N(CH_3)_2$ | Cl, Cl | |
| 45 | $C_6H_5$ | $-O-CO-N(CH_3)OCH_3$ | Cl, Cl | |
| 46 | $C_6H_5$ | $-O-SO_2-CH_3$ | Cl, Cl | |
| 47 | $C_6H_5$ | $-O-SO_2-CF_3$ | Cl, Cl | |
| 48 | $C_6H_5$ | $-O-CO-OCH_3$ | Cl, Cl | |
| 49 | $C_6H_5$ | $-SCH_3$ | Cl, Cl | m.p. 96–98° C. |
| 50 | $C_6H_5$ | $-S-CO-CH_3$ | Cl, Cl | |
| 51 | $C_6H_5$ | $-S-CN$ | Cl, Cl | |
| 52 | $C_6H_5$ | SH | Cl, Cl | |
| 53 | $C_6H_5$ | $-S-CO-N(CH_3)-OCH_3$ | Cl, Cl | |
| 54 | $C_6H_5$ | $-S-C_3H_7-n$ | Cl, Cl | |
| 55 | $4-OCH_3-C_6H_4-$ | $NH_2$ | Cl, Cl | |
| 56 | $3-OCH_3-C_6H_4-$ | $N(CH_3)_2$ | Cl, Cl | |
| 57 | $4-F-C_6H_4-$ | $OCH_3$ | Cl, Cl | |
| 58 | $4-F-C_6H_4-$ | OH | Cl, Cl | |
| 59 | $4-F-C_6H_4-$ | $O-CO-CH_3$ | Cl, Cl | |
| 60 | $3-OCH_3-C_6H_4-$ | $OCH_3$ | Cl, Cl | m.p. 113–115° C. |
| 61 | $3-OH-C_6H_4-$ | OH | Cl, Cl | |
| 62 | $3-CH_3-C_6H_4-$ | $NH_2$ | Cl, Cl | |
| 63 | $3-CH_3-C_6H_4-$ | $NH-CO-CH_3$ | Cl, Cl | |
| 64 | $3-CH_3-5-CH_3-C_6H_3-$ | $NH-CH_3$ | Cl, Cl | |
| 65 | $3-CH_3-5-CH_3-C_6H_3-$ | $NH-CO-OCH_3$ | Cl, Cl | |
| 66 | $4-HC\equiv C-C_6H_4-$ | $OCH_3$ | Cl, Cl | |
| 67 | $3-Cl-C_6H_4-$ | $-NH-CH_2-C\equiv CH$ | Cl, Cl | |
| 68 | $3-Cl-4-F-C_6H_3-$ | $SCH_3$ | Cl, Cl | |
| 69 | $4-HOOC-C_6H_4$ | $NH_2$ | Cl, Cl | |
| 70 | $4-CH_3-CO-C_6H_4-$ | $-N(CH_3)_2$ | Cl, Cl | |
| 71 | $3-NO_2-C_6H_4-$ | $OCH_3$ | Cl, Cl | |
| 72 | $3-NO_2-C_6H_4-$ | OH | Cl, Cl | |
| 73 | $3-NH_2-C_6H_4-$ | OH | Cl, Cl | |
| 74 | $3-CH_3-CO-NH-C_6H_4-$ | $-O-CO-CH_3$ | Cl, Cl | |
| 75 | $4-OH-C_6H_4$ | OH | Cl, Cl | |
| 76 | $4-OCH_3-C_6H_4-$ | $OCH_3$ | Cl, Cl | |
| 77 | $4-CH_3-NH-CO-O-C_6H_4-$ | $-O-CO-NH-CH_3$ | Cl, Cl | |
| 78 | $3-OCH_3-4-OCH_3-5-OCH_3-C_6H_2-$ | $NH_2$ | Cl, Cl | |
| 79 | $3-OCH_3-4-OCH_3-5-OCH_3-C_6H_2-$ | $-NH-SO_2-CF_3$ | Cl, Cl | |
| 80 | $3-Cl-4-Cl-C_6H_3-$ | $-O-C_4H_9-n$ | Cl, Cl | |
| 81 | $4-N(CH_3)_2-C_6H_4-$ | $-O-CO-CH_2Cl$ | Cl, Cl | |

TABLE 1-continued

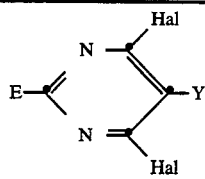

| No. | E | Y | Hal | Physical data |
|---|---|---|---|---|
| 82 | 2-OCH$_3$—C$_6$H$_4$— | N—pyrrolidinyl | Cl, Cl | |
| 83 | C$_6$H$_5$ | OH | Br, Br | |
| 84 | C$_6$H$_5$ | NH$_2$ | Br, Br | m.p. 126–129° C. |
| 85 | 4- | OH | Br, Br | |
| 86 | C$_6$H$_5$ | OH | Br, Cl | |
| 87 | C$_6$H$_5$ | OCH$_3$ | Br, Br | m.p. 88–89° C. |
| 88 | 4-F—C$_6$H$_4$— | NH$_2$ | Br, Br | |
| 89 | C$_6$H$_5$ | NH$_2$ | F, Cl | |
| 90 | 4-CH$_3$—C$_6$H$_4$— | —O—CO—CH$_3$ | Br, Br | |
| 91 | 2-thienyl | NH$_2$ | Cl, Cl | |
| 92 | 3-thienyl | OH | Cl, Cl | |
| 93 | 2-furyl | NH$_2$ | Cl, Cl | m.p. 139–140° C. |
| 94 | H$_2$N-(4-methyl-2-thienyl) | NH$_2$ | Cl, Cl | m.p. 160° (decomp.) |
| 95 | (5-chloro-2-thienyl) | —O—CO—NH—CH$_3$ | Cl, Cl | |
| 96 | 3-furyl | —N(CH$_3$)$_2$ | Cl, Cl | |
| 97 | 3-thienyl | OCH$_3$ | Br, Br | |
| 98 | 2-furyl | OCH$_3$ | Cl, Cl | |
| 99 | 2-furyl | OH | Cl, Cl | |
| 100 | 2-furyl | OCH$_3$ | Cl, Cl | m.p. 109–111° C. |
| 101 | C$_6$H$_5$ | —N(CHONHC$_6$H$_5$)$_2$ | Cl, Cl | amorphous m.p. >230° C. |
| 102 | 4-tolyl | OCH$_3$ | Cl, Cl | m.p. 109–111° C. |
| 103 | 4-tolyl | —NH$_2$ | Cl, Cl | m.p. 150–152° C. |
| 104 | 4,6-(Cl)$_2$C$_6$H$_3$— | NH$_2$ | Cl, Cl | m.p. 199° C. |
| 105 | 3-OCH$_3$C$_6$H$_4$— | NH$_2$ | Cl, Cl | solid |
| 106 | 4-tolyl | OH | Cl, Cl | m.p. 133–135° C. |
| 107 | 3-ClC$_6$H$_4$— | NH$_2$ | Cl, Cl | m.p. 168–170° C. |
| 108 | 4-ClC$_6$H$_4$— | OCH$_3$ | Cl, Cl | m.p. 136° |
| 109 | C$_6$H$_5$ | N(C$_2$H$_5$)$_2$ | Cl, Cl | $n_D^{27}$ 1.6012 |
| 110 | 4-CH$_3$—3NO$_2$C$_6$H$_3$— | NH$_2$ | Cl, Cl | m.p. 212–214° C. |
| 111 | 4-CH$_3$—3NH$_2$—C$_6$H$_5$ | NH$_2$ | Cl, Cl | m.p. 167–168° C. |

FORMULATION EXAMPLES

The compounds of the formula I are generally not used as such in agriculture but are incorporated into ready-for-use compositions which can be applied either directly or diluted with water.

EXAMPLE 6

Dusts

The following substances are used to produce (a) a 5% dust and (b) a 2% dust:

| | |
|---|---|
| a | 5 parts of 5-amino-4,6-dichloro-2-phenylpyrimidine or of a mixture thereof with 2-chloro-2',6'-diethyl-N—(butoxymethyl)-acetanilide, |
| | 95 parts of talcum, |
| b | 2 parts of the above active ingredient or of a mixture thereof, |
| | 1 part of highly dispersed silicic acid, |
| | 97 parts of talcum. |

The active ingredients are mixed and ground with the carriers, and can be applied in this form.

EXAMPLE 7

Granulate

The following substances are used to produce a 5% granulate:

| |
|---|
| 5 parts of 4,6-dichloro-5-hydroxy-2-phenylpyrimidine or of a mixture thereof with 2-chloro-2',6'-diethyl-N—(methoxymethyl)-acetanilide, |
| 0.25 part of expoxidised vegetable oil, |
| 0.25 part of cetyl polyglycol ether, |
| 3.50 parts of polyethylene glycol, and |
| 91 parts of kaolin (particle size 0.3–0.8 mm). |

The active substance or the mixture is mixed with the vegetable oil, and the mixture obtained is dissolved in 6 parts of acetone, after which the polyethylene glycol and the cetyl polyglycol ether are added. The resulting solution is sprayed onto kaolin, and the acetone is subsequently evaporated off in vacuo. A microgranulate of this kind is advantageously worked into seed furrows.

EXAMPLE 8

Wettable powders

The following constituents are used to produce wettable powders containing (a) 70%, (b) 40%, (c) 25%, (d) 25% and (e) 10% of active ingredient:

| | |
|---|---|
| a | 70 parts of 4,6-dichloro-5-methoxy-2-phenylpyrimidine or of a mixture thereof with 2-chloro-2',6'-diethyl-N—(2''-propoxyethyl)-acetanilide, |
| | 5 parts of sodium dibutylnaphthalene sulfonate, |
| | 3 parts of naphthalenesulfonic acid/phenolsulfonic acid/formaldehyde condensate (3:2:1), |
| | 10 parts of kaolin, and |
| | 12 parts of Champagne chalk; |
| b | 40 parts of active ingredient or of a mixture as above, |
| | 5 parts of sodium lignin sulfonate, |
| | 1 part of sodium dibutylnaphthalene sulfonate, and |
| | 54 parts of silicic aci |
| c | 25 parts of active ingredient or of a mixture as above, |
| | 4.5 parts of calcium lignin sulfonate, |
| | 1.9 parts of Champagne chalk/hydroxyethyl cellulose mixture (1:1), |
| | 1.5 parts of sodium dibutylnaphthalene sulfonate, |
| | 19.5 parts of silicic acid, |
| | 19.5 parts of Champagne chalk, and |
| | 28.1 parts of kaolin; |
| d | 25 parts of active ingredient or of a mixture as above, |
| | 2.5 parts of isooctylphenoxy-polyoxyethylene-ethanol, |
| | 1.7 parts of Champagne chalk/hydroxyethyl cellulose mixture (1:1), |
| | 8.3 parts of sodium aluminium silicate, |
| | 16.5 parts of kieselguhr, and |
| | 46 parts of kaolin; and |
| e | 10 parts of active ingredient or of a mixture as above, |
| | 3 parts of a mixture of the sodium salts of saturated fatty alcohol sulfates, |
| | 5 parts of naphthalenesulfonic acid/formaldehyde condensate, and |
| | 82 parts of kaolin. |

The active ingredients are intimately mixed in suitable mixtures with the additives, and the mixture is ground in appropriate mills and rollers. Wettable powders having excellent wetting and suspension properties are obtained. These wettable powders can be diluted with water to obtain suspensions of the concentration required, and in this form they are suitable in particular for leaf application.

EXAMPLE 9

Emulsifiable concentrate

The following substances are used to produce a 25% emulsifiable concentrate:

| |
|---|
| 25 parts of 4,6-dichloro-5-hydroxy-2-phenylpyrimidine or of a mixture thereof with 2-chloro-6'-ethyl-N—(2''-methoxy-1''-methylethyl)-acet-o-toluidide, |
| 10 parts of an alkylarylsulfonate/fatty alcohol polyglycol ether mixture, |
| 5 parts of dimethylformamide, and |
| 57.5 parts of xylene. |

EXAMPLE 10

Pastes

The following substances are used to produce a 45% paste:

| | |
|---|---|
| a | 45 parts of 4,6-dichloro-5-methoxy-2-phenylpyrimidine or of a mixture thereof with 2-chloro-2',6'-diethyl-N—(methoxymethyl)-acetanilide, |
| | 5 parts of sodium aluminium silicate, |
| | 14 parts of cetyl polyethylene glycol ether having 8 mols of ethylene oxide, |
| | 1 part of oleyl polyethylene glycol ether having 5 mols of ethylene oxide, |
| | 2 parts of spindle oil, |
| | 23 parts of water, and |
| | 10 parts of polyethylene glycol; and |
| b | 45 parts of the above active ingredient or of a mixture thereof as above, |
| | 5 parts of ethylene glycol, |
| | 3 parts of octylphenoxypolyethylene glycol having 9-10 mols of ethylene oxide per mol of octylphenol, |
| | 3 parts of a mixture of aromatic sulfonesulfonic acids, condensed with formaldehyde as ammonium salt, |
| | 1 part of silicone oil in the form of a 75% emulsion, |
| | 0.1 part of a mixture of 1-(3-chloroallyl)-3m5m7-triazoazonium-adamantane chloride with sodium carbonate, chloride value at least 11.5%, |
| | 0.2 part of a biopolymeric thickener having a maximum of 100 nuclei per gram, and |
| | 42.7 parts of water. |

The active ingredient is intimately mixed and ground with the additives in suitable devices. There is obtained a paste from which suspensions of the concentration required can be produced by dilution with water.

BIOLOGICAL EXAMPLES

The capability of the compounds of the formula I to protect cultivated plants against the action of strong herbicides can be seen from the following Example. In the test descriptions, the compounds of the formula I are designated as antidotes. The relative protective action is given in %.

EXAMPLE 11

Test with antidote and herbicide on rice sown in water

Application of the antidote during soaking of the rice seeds

Rice seeds are soaked during 48 hours in solutions of 100 ppm of the substance to be tested as antidote. The seeds are subsequently left to dry for about 2 hours until they are no longer sticky. Plastics containers (25 cm long, 17 cm wide and 12 cm high) are filled with sandy loam to within 2 cm of the top edge. The pre-soaked seeds are sown on the surface of the soil in each container, and are covered over with a small amount of soil. The soil is kept in a moist (not boggy) conditions, and the herbicide is sprayed as a dilute solution onto the surface of the soil. The level of water is successively raised to correspond to the growth of the plants. The relative protective action of the antidote is estimated in percent 21 days after sowing. Reference values are provided by the plants treated with the herbicide alone (no protective action), and by the completely untreated control plants (100% growth). The results are summarised in the Table which follows.

The herbicide used is 2-chloro-2',6'-diethyl-N-(2"-propyloxyethyl)-acetanilide ("Pretilachlor"), and the amount applied is 0.25 kg per hectare.

| Antidote No. | Relative protective action |
|---|---|
| 1 | 50% |
| 3 | 12,5% |
| 10 | 12,5% |
| 11 | 12,5% |
| 42 | 12,5% |
| 60 | 38% |
| 84 | 63% |
| 94 | 50% |
| 104 | 50% |
| 105 | 63% |
| 107 | 38% |
| 108 | 50% |
| 109 | 12,5% |

EXAMPLE 12

Test with antidote and herbicide on rice sown in water (The rice seeds are pre-soaked and are sown directly into very wet, bog-like or flooded soils. Application of the antidote as tank-mixture)

Rice seeds are pre-soaked for 48 hours. Plastics containers (25 cm long, 17 cm wide and 12 cm high) are filled with soil, into which the pre-soaked seeds are shown. The substance to be tested as antidote together with the herbicide is then sprayed as tank mixture onto the soil. The level of the water is successively raised to correspond to the growth of the rice plants. The protective action of the antidote is estimated in percent 21 days after sowing. Reference values are provided by the plants treated with the herbicide alone (no protective action), and by the completely untreated plants (100% growth). The results are summarised below.

The herbicide used is 2-chloro-2",6"-diethyl-N-(2"-propyloxyethyl)-acetanilide ("Pretilachlor").

| Antidote No. | Applied amount | Applied amount of herbicide | Relative protective action |
|---|---|---|---|
| 1 | 1 kg/ha | 1 kg/ha | 63% |
| 1 | 0,5 kg/ha | 0,5 kg/ha | 50% |
| 84 | 1 kg/ha | 1 kg/ha | 25% |
| 84 | 0,5 kg/ha | 0,5 kg/ha | 30% |
| 103 | 1 kg/ha | 1 kg/ha | 25% |
| 103 | 0,5 kg/ha | 0,5 kg/ha | 25% |
| 104 | 0,5 kg/ha | 0,5 kg/ha | 25% |
| 105 | 1 kg/ha | 1 kg/ha | 63% |
| 105 | 0,5 kg/ha | 0,5 kg/ha | 63% |
| 108 | 0,5 kg/ha | 0,5 kg/ha | 50% |

EXAMPLE 13

Test with antidote and herbicide on transplanted rice

Application of antidote and herbicide as tank mixture in the pre-emergence process Rice plants are grown to the 1½-leaf stage in soil. The plants are then transplanted in bunches (always 3 plants together) into sandy loam in containers (47 cm long, 29 cm wide and 24 cm high). The surface of the soil is subsequently covered with water to a depth of 1.5-2 cm. Two to three days after transplantation, the herbicide together with the substance to be tested as antidote is applied directly as tank mixture into the water. The protective action of the antidote is estimated in percent 24 days after transplantation. Reference values are provided by the plants treated with the herbicide alone (no protective action), and by the completely untreated control plants (100% growth). The results are summarised below.

The herbicide used is 2-chloro-2",6"-diethyl-N-(2"-propyloxyethyl)-acetanilide ("Pretilachlor").

| Antidote No. | Applied amount | Applied amount of herbicide | Relative protective action |
|---|---|---|---|
| 1 | 1 kg/ha | 1 kg/ha | 38% |
| 1 | 0,5 kg/ha | 1 kg/ha | 25% |
| 1 | 0.75 kg/ha | 0.75 kg/ha | 38% |
| 1 | 0.375 kg/ha | 0.75 kg/ha | 38% |

EXAMPLE 14

Test with antidote and herbicide on dry-sown rice

Application of the antidote as seed dressing

Rice seeds are mixed with the substance to be used as antidote (safener) in a glass container. Seeds and product are well mixed together by shaking and rotation. Containers (47 cm long, 29 cm wide and 24 cm high) are then filled with sandy loam, and the dressed seeds are sown therein. After the seeds have been covered, the herbicide in dilute solution is sprayed onto the surface of the soil. About 20 days after sowing (3-leaf stage of the rice plants), plants), the surface of the soil is covered to a depth of 4 cm with water. Thirty days after application of the herbicide, the protective action of the antidote is estimated in percent. Reference values are provided by plants treated with the herbicide alone (no protective action), and also by the completely untreated control plants (100% growth). The results are summarised below.

Herbicide:

2-Chloro-2'-ethyl-6-methyl-N-(2"-methoxy-1"-methylethyl)-acetanilide ("Metalochlor").

| Antidote No. | Applied amount | Applied amount of herbicide | Relative protective action |
|---|---|---|---|
| 1 | 0,5 g/kg of seed | 0,5 kg/ha | 38% |
| 1 | 0,5 g/kg of seed | 0,25 kg/ha | 25% |

EXAMPLE 15

Test with antidote and herbicide on rice: application of the antidote as seed dressing Rice seeds are mixed together in a glass container with the substance to be used as antidote. Seeds and product are well mixed together by shaking and rotation. Plastics containers (47 cm long, 29 cm wide and 24 cm high) are filled with sandy loam, and the dressed seeds are sown therein. After the seeds have been covered, the herbicide is sprayed onto the surface of the soil. The protective action of the antidote is estimated in percent 18 days after sowing. Reference values are provided by the plants treated with herbicide alone (no protective action), and also by the completely untreated control plants (=100% growth). The results are summarised below.

Herbicide:

2-Chloro-2'-ethyl-6'-methyl-N-(1'-methoxy-1'-methylethyl)-acetanilide ("Metolachlor").

| Antidote No. | Applied amount | Herbicide applied amount | Relative protective action |
| --- | --- | --- | --- |
| 1 | 0.5 g/kg of seed | 0.5 kg/ha | 38% |
| 1 | 0.5 g/kg of seed | 0.25 kg/ha | 25% |

EXAMPLE 16

Test with antidote and herbicide on sorghum (millet)

Application of herbicide and antidote as tank mixture in the pre-emergence process Pots having an upper diameter of 6 cm are filled with sandy loam soil, and sorghum seeds of the G522 variety are sown therein. After the seeds have been covered, the substance to be tested as antidote together with the herbicide is sprayed in dilute solution as tank mixture onto the surface of the soil. The protective action of the antidote is estimated in percent 21 days after the application of the herbicide. Reference values are provided by the plants treated with the herbicide alone (no protective action), and also by the completely untreated control plants (=100% growth). The results are summarised below.

Herbicide:
2-Chloro-2'-ethyl-6'-methyl-N-(2''-methoxy-2''-methylethyl)-acetanilide ("Metolachlor").

| Antidote No. | Applied amount | Herbicide applied amount | Relative protective action |
| --- | --- | --- | --- |
| 104 | 1.5 kg/ha | 1.5 kg/ha | 50% |

What is claimed is:

1. A 2-aryl-4,6-dihalopyrimidine of the formula

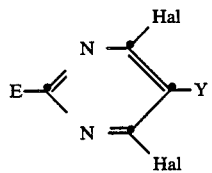

wherein
E is a group

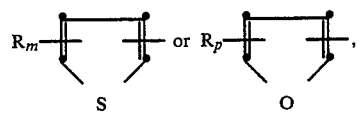

each Hal independently of the other is halogen,
Y is a group: $-NR^1R^2$, $OR^3$, $-N=CR^4R^5$, $-N=CH-NR^6R^7$,
R is halogen, nitro, $-OR^8$, $-NR^9R^{10}$, $-CO-R^{11}$, $-COOR^{11}$, $-CO-NR^9R^{10}$, $-O-CO-N(R^{11})-OR^{11}$, a $C_1-C_6$alkyl or $C_3-C_6$-cycloalkyl group each unsubstituted or substituted by halogen, or it is a $C_2-C_6$-alkeynl or $C_2-C_6$-alkynyl group
m and p are zero or a number from one to two,
$R^1$, $R^2$ and $R^3$ independently of one another are each hydrogen, $-SO_2-C_1-C_6$-alkyl, $-SO_2-C_1-C_6$-haloalkyl, $-COR^4$, or $C_1-C_6$-alkyl or $C_3-C_6$-alkenyl, except that $R^3$ may not be hydrogen,
$R^4$ and $R^5$ independently of one another are hydrgen, $C_3-C_6$-alkynyl, or $C_1-C_6$-alkyl or $C_3-C_6$-alkenyl each substituted or substituted by halogen or $C_1-C_4$-alkoxy,
$R^6$ and $R^7$ independently of one another are each $C_1-C_6$-alkyl which is unsubstituted or substituted by halogen,
$R^8$ is hydrogen, $C_1-C_6$-alkylcarbonyl, $C_3-C_6$-alkenylcarbonyl, $C_3-C_6$-alkynylcarbonyl, or a $C_1-C_6$-alkyl $C_3-C_6$-alkenyl or $C_3-C_6$-alkynyl group each unsubstituted or substituted by halogen, hydroxyl, $C_1-C_4$-alkoxy or $-NR^9R^{10}$,
$R^9$ and $R^{10}$ independently of one another are each hydrogen, $C_3-C_6$-alkenyl, $C_3-C_6$-alkynyl, $C_3-C_6$-cycloalkyl or $C_1-C_6$-alkyl
$R^{11}$ is hydrogen or a $C_1-C_6$-alkyl, $C_3-C_6$-alkynyl group, and halogen, as used herein, is selected from fluorine, chlorine, and bromine.

2. A composition for protecting cultivated plants against herbicides which composition contains as active ingredient an effective amount of a 2-aryl-4,6-dihalopyrimidine of claim 1, together with inert carriers and additives.

3. A composition according to claim 2, which contains
   (a) a herbicidally effective chloroacetanilide and
   (b) a 2-aryl-4,6-dihalopyrimidine according to claim 1 as antidote.

4. A process for protecting cultivated plants against the harmful action of a herbicide, which process comprises the step of applying an effective amount of a 2-aryl-4,6-dihalopyrimidine of claim 1 to the plants, to the seeds of the plants, or to the locus thereof.

5. A process according to claim 4, wherein the cultivated plants are cereals, maize or sorghum, and the herbicide is a chloroacetanilide herbicide.

6. A process according to claim 5, wherein the cereal plants are rice plants.

7. A process according to claim 4 for protecting cultivated plants against damage which could otherwise occur on application of herbicides, which process comprises treating the cultivated area for the plants before or during application of the herbicide with an effective amount of the 2-aryl-4,6-dihalopyrimidine.

8. A process according to claim 4 for protecting cultivated plants against damage which could otherwise occur on application of herbicides, which process comprises treating the seeds or the seedlings of the plants or the plants themselves with an effective amount of the 2-aryl-4,6-dihalopyrimidine.

9. A 2-aryl-4,6-dihalopyrimidine of the formula

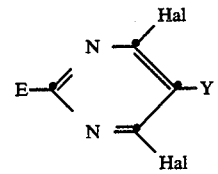

wherein
E is

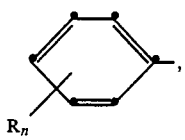

each Hal independently of the other is halogen,
Y is a group: $-NR^1R^2$, $-OR^3$, $-N=CR^4R^5$, $-N=CH-NR^6R^7$, R is halogen, nitro, $-OR^8$, $-NR^9R^{10}$, $-CO-R^{11}$, $-COOR^{11}$, $-CO-NR^9R^{10}$, $-O-CO-N(R^{11})-OR^{11}$, a $C_1-C_6$alkyl or $C_3-C_6$-cycloalkyl group each unsubstituted or substituted by halogen, or it is a $C_2-C_6$-alkenyl or $C_2-C_6$-alkynyl group, n is zero or a number from one to three, $R^1$, $R^2$ and $R^3$ independently of one another are each hydrogen, $-SO_2-C_1-C_6$-alkyl, $-SO_2-C_1-C_6$-haloalkyl, $-COR^4$, or $C_1-C_6$-alkyl or $C_3-C_6$-alkenyl, except that $R^3$ may not be hydrogen, $R^4$ and $R^5$ independently of one another are hydrogen, $C_3-C_6$-alkynyl, or $C_1-C_6$-alkyl or $C_3-C_6$-alkenyl each unsubstituted or substituted by halogen or $C_1-C_4$-alkoxy, $R^6$ and $R^7$ independently of one another are each $C_1-C_6$-alkyl which is unsubstituted or substituted by halogen, $R^8$ is hydrogen, $C_1-C_6$-alkylcarbonyl, $C_3-C_6$-alkenylcarbonyl, $C_3-C_6$-alkynylcarbonyl, or a $C_1-C_6$-alkyl $C_3-C_6$-alkenyl or $C_3-C_6$-alkynyl group each unsubstituted or substituted by halogen, hydroxy, $C_1-C_4$-alkoxy or $-NR^9R^{10}$, $R^9$ and $R^{10}$ independently of one another are each hydrogen, $C_3-C_6$-alkenyl, $C_3-C_6$-alkynyl, $C_3-C_6$-cycloalkyl or $C_1-C_6$-alkyl, $R^{11}$ is hydrogen or a $C_1-C_6$-alkyl, $C_3-C_6$-alkenyl or $C_3-C_6$-alkynyl group, and halogen, as used herein, is selected from fluorine, chlorine, and bromine.

10. A compound according to claim 9, wherein E is the group

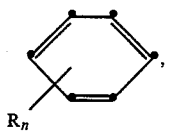

p is a zero one or two, and
R is halogen, nitro, $OR^8$, $-NR^9R^{10}$, $-CO-R^{11}$, $-CO-NR^9R^{10}$, $C_1-C_4$-alkyl, $C_2-C_4$-alkenyl or $C_2-C_4$-alkynyl.

11. A compound according to claim 9, wherein E is the phenyl nucleus which is unsubstituted or monosubstituted by methoxy, fluorine, hydroxyl, methyl, ethynyl, carboxyl, acetyl, nitro, amino, dimethylamino, acetamido or methylaminocarbonyloxy, or is disubstituted by fluorine or chlorine, or is trisubstituted by methoxy, Hal is chlorine or bromine, and Y is $-NR^1R^2$, $-OR^3$, $-N=N-NR^6R^7$ or $-N=CR^4R^5$.

12. A compound according to claim 9, wherein E is the phenyl nucleus which is unsubstituted or monosubstituted by methoxy, fluorine, hydroxyl, methyl, ethynyl, carboxyl, acetyl, nitro, amino, dimethylamino, acetamido or methylaminocarbonyloxy, or is disubstituted by flourine or chlorine, or is trisubstituted by methoxy, and Hal is chlorine or bromine.

13. A compound according to claim 9, wherein E is the phenyl nucleus, Hal is chlorine, and Y is $-NR_1R_2$.

14. A compound according to claim 9, wherein E is the phenyl nucleus, Hal is chlorine, and Y is amino, dimethylamino, diacetamido, trifluoroacetamido, hydroxyl, methoxy, methylthio, acetoxy, acetamido or methylaminocarbonyloxy.

15. 5-Amino-4,6-dichloro-2-phenylpyrimidine according to claim 9.

16. 5-Amino-4,6-dichloro-2-(3'-methoxyphenyl)-pyrimidine according to claim 9.

17. 5-(N,N-Di-(phenoxycarbamoyl)-amino-4,6-dichloro-2-phenylpyrimidine according to claim 9.

18. 5-Amino-4,6-dibromo-2-phenylpyrimidine according to claim 9.

19. A composition for protecting cultivated plants against herbicides, which composition contains, as an activeingredient, an effective amount of a 2-aryl-4,6-dihalopyrimidine according to claim 9 together with inert carriers and additives.

20. A composition according to claim 19 which contains (a) a herbicidally effective chloroacetanilide and
(b) said 2-aryl-4,6-dihalopyrimidine as antidote.

21. A process for protecting cultivated plants against the harmful action of a herbicide, which process comprises the step of applying an effective amount of said 2-aryl-4,6-dihalopyrimidine of claim 9 to the plants, to the seeds of the plants, or to the locus thereof.

22. A process according to claim 21 wherein the cultivated plants are cereals, maize, or sorghum and the herbicide is a chloracetanilide herbicide.

23. A process according to claim 22 wherein the cereal plants are rice plants.

24. A process according to claim 21 for protecting cultivated plants against damage which could otherwise occur on application of herbicides, which process comprises treating the cultivated area for the plants before or during application of the herbicide with an effective amount of said 2-aryl-4,6-dihalopyrimidine.

25. The process of claim 21 for protecting cultivated plants against damage which could otherwise occur on application of herbicides, which process comprises treating the seeds or the seedlings of the plants or the plants themselves with an effective amount of the 2-aryl-4,6-dihalopyrimidine.

* * * * *